US011462333B1

(12) United States Patent
Lev et al.

(10) Patent No.: US 11,462,333 B1
(45) Date of Patent: Oct. 4, 2022

(54) TELEMEDICAL APPARATUS, SYSTEM, AND METHOD FOR PROVIDING MEDICAL SERVICES REMOTELY

(71) Applicants: Bruce A. Lev, Peoria, AZ (US); Brandon E. Lev, Peoria, AZ (US); Amaya S. Lev, Peoria, AZ (US); Arianna B. Lev, Peoria, AZ (US)

(72) Inventors: Bruce A. Lev, Peoria, AZ (US); Brandon E. Lev, Peoria, AZ (US); Amaya S. Lev, Peoria, AZ (US); Arianna B. Lev, Peoria, AZ (US)

( * ) Notice: Subject to any disclaimer, the term of this patent is extended or adjusted under 35 U.S.C. 154(b) by 548 days.

(21) Appl. No.: 16/553,307

(22) Filed: Aug. 28, 2019

Related U.S. Application Data

(63) Continuation-in-part of application No. 12/387,948, filed on May 11, 2009.

(51) Int. Cl.
| | |
|---|---|
| *G16H 80/00* | (2018.01) |
| *A61B 5/00* | (2006.01) |
| *G16H 50/20* | (2018.01) |
| *A61M 21/02* | (2006.01) |
| *G16H 10/60* | (2018.01) |

(Continued)

(52) U.S. Cl.
CPC .......... *G16H 80/00* (2018.01); *A61B 5/0022* (2013.01); *G16H 10/20* (2018.01); *G16H 10/60* (2018.01); *G16H 20/10* (2018.01); *G16H 20/70* (2018.01); *G16H 40/67* (2018.01); *G16H 50/20* (2018.01); *A61B 5/0006* (2013.01);

(Continued)

(58) Field of Classification Search
CPC ...................... A61M 2230/005; A61M 21/02; G16H 40/67; G16H 50/20; G16H 80/00; G16H 10/20; G16H 10/60; G16H 20/70; A61B 5/0002; A61B 5/4836; A61B 5/0022

See application file for complete search history.

(56) References Cited

U.S. PATENT DOCUMENTS 5,410,471 A * 4/1995 Alyfuku .................... A61B 5/20
600/300
5,810,747 A * 9/1998 Brudny .................. A61B 5/002
434/350

(Continued)

*Primary Examiner* — Christine H Matthews
(74) *Attorney, Agent, or Firm* — Bruce A. Lev

(57) ABSTRACT

A telemedical apparatus, system, and method for providing medical services to a patient remotely using electronic communications. The apparatus, system, and method includes a primary computer module having data input mechanisms, a secondary computer module including data receiving, interpreting, and diagnosing capabilities remotely located from the primary computer module, electronic communication devices between the primary computer module and the secondary computer module, a mechanism for relaxation connected to the primary computer module and adapted to stabilize a patient's biological vital signs before the biological vital signs information is collected and sent by the primary computer module, at least one medical component adapted to obtain and send biological vital sign information of the patient to the primary computer module; and a mechanism for receiving and printing medical prescriptions connected to the primary computer module, wherein the secondary computer module is capable of sending medical prescriptions and the primary computer module is capable of receiving and printing medical prescriptions.

33 Claims, 8 Drawing Sheets

(51) Int. Cl.
- *G16H 10/20* (2018.01)
- *G16H 40/67* (2018.01)
- *G16H 20/10* (2018.01)
- *G16H 20/70* (2018.01)
- G16H 40/40 (2018.01)
- G16H 20/30 (2018.01)

(52) U.S. Cl.
CPC ............ *A61B 5/0008* (2013.01); *G16H 20/30* (2018.01); *G16H 40/40* (2018.01)

(56) References Cited

U.S. PATENT DOCUMENTS

| | | | |
|---|---|---|---|
| 6,046,761 A | 4/2000 | Echerer | |
| 6,409,660 B1 | 6/2002 | Sjoqvist | |
| 8,500,636 B2 | 8/2013 | Tran | |
| 8,589,177 B2 | 11/2013 | Haq | |
| 9,224,180 B2 | 12/2015 | Macoviak et al. | |
| 2004/0077934 A1* | 4/2004 | Massad | A63F 9/24 128/903 |
| 2005/0124851 A1* | 6/2005 | Patton | A61B 5/486 600/26 |
| 2006/0020161 A1* | 1/2006 | Mageras | A61M 21/00 600/28 |
| 2006/0293572 A1* | 12/2006 | Bulat | H04N 7/147 600/300 |
| 2010/0205742 A1* | 8/2010 | Stone | A61G 15/02 5/617 |

\* cited by examiner

TELEMEDICAL APPARATUS, SYSTEM, AND METHOD FOR PROVIDING MEDICAL SERVICES REMOTELY

CROSS-REFERENCE TO RELATED APPLICATION

The present application is related to and claims priority from prior application Ser. No. 12/387,948, filed May 11, 2009 which is incorporated herein by reference.

COPYRIGHT NOTICE

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever. 37 CFR 1.71(d).

BACKGROUND OF THE INVENTION

Field of the Invention

This invention relates to telemedical apparatuses, systems, and methods for providing medical services to a patient remotely using electronic communications and equipment, biological vital signs and personal information, and available medical practitioners.

Background

There are numerous instances and situations when a person needs medical attention and care but is either too far away from such services and providers or the attention and care needed is not urgent and can be serviced remotely and conveniently using an apparatus, system, and method as described herein.

In the past, a person needing medical attention and care would need to schedule an appointment with a practitioner, commute to that practitioner's location, wait in a waiting room for a period of time, and fill in forms and paperwork by hand before receiving even a basic examination. It became obvious that a need existed to incorporate available technologies into an apparatus, system, and method that could provide these services remotely and electronically.

Further, it has been proven in numerous medical tests, trials, and actual cases that a person in a calm or relaxed state will display more accurate and informative vital signs than those that are agitated, tired, anxious, frustrated, confused, etc. When a patient first arrives at a telemedical apparatus of the prior art they may be unsure and anxious as to what to expect from the apparatus or the lack thereof of a professional doctor or nurse being there in person to offer a personal touch, they may be agitated by their previous daily events, they may be tired by their commute to the telemedical module, etc. Therefore, it is extremely important that vital signs taken remotely be preceded by a mechanism, means, or method for relaxation to thereby improve the quality and accuracy of the vital signs retrieved, the analyses and diagnosis calculated, and the advice and services thereby rendered.

Within the configuration of the instant invention, a chosen relaxation mechanism, means, or method accompanies and communicates with the computer module in a convenient location for a patient to connect with quickly, easily, and comfortably. This relaxation mechanism, means, or method can be formed in many configurations, such as providing a comfortable seat formed as a chair or recliner, handles that include hand vibrators and/or hand warmers that can be attached to each vertical side of the module, a head set that vibrates and cools a patient's head, an odorizer that produces a pleasant smell, a noise generator that plays pleasant tones or music, offering meditation techniques, offering progressive neuromuscular relaxation techniques, offering message therapy, offering medicinal therapy, offering sex therapy, offering hypnosis techniques and methods, providing a misting mechanism, providing a virtual reality mechanisms, providing a tickling mechanisms, providing reading materials, providing mechanisms to induce sleep, providing mechanisms to induce laughter, providing musical instruments, providing athletics devices, providing mechanisms for urinating and/or defecating, providing a water tank for a patient to lay and relax in, providing biofeedback mechanisms, and/or any similar means, mechanisms, or methods, or combinations of any thereof.

Another deficiency of current telemedical designs and apparatuses is that once a patient has been diagnosed and medical treatment and services been determined there is no convenient mechanism, means, or method to deliver a prescription to the remote patient nor to fill the prescription by that patient. The instant invention overcomes these deficiencies by providing a mechanism for receiving and printing a prescription which can then be carried by the patient to a convenient or local pharmacy to fill. The mechanism for receiving and printing a prescription can be formed as a combination of facsimile software within the computer module and a small printing mechanism communicating with the computer module. The mechanism can also be formed using digital files created by a medical professional and sent electronically to the computer module to be stored or printed. Or any equivalent or obvious variations thereof. Therefore, a prescription can be written by a medical professional, sent electronically to the computer module, printed by the printing mechanism, obtained by the patient, taken by the patient to a convenient or local pharmacy, and filled by said pharmacy.

A variation of the prescription filling mechanism, means, or method would be to have a chosen pharmacy or pharmacies integrated within the telemedical system that could be adapted and capable of receiving the patient's determined prescription directly and then filling that prescription for the patient. The patient could then either pick up the prescription in person or have the prescription delivered to a desired location chosen.

Description of the Prior Art

Other apparatuses, systems, and methods have been developed to accomplish some of these telemedical functions and requirements, including the system of Echerer, U.S. Pat. No. 6,046,761. The system of Echerer does include medical components that do accomplish basic telemedical functions. However, there are no mechanisms, means, or methods within the Echerer system that will relax a patient or better well prepare them for the reading of their vital signs. As such, the readings taken may not be accurate and the medical advice and services rendered thereof may not be accurate or helpful. In fact, the numerous steps that Echerer uses before taking the patient's vital signs, for example, verifying the identity of the patient by asking them to hold up an identification card to the system's video camera and determining an acceptable mode of payment, may actually increase the patient's stress levels and cause further inaccuracies within the readings of their vital signs.

Another improvement over the system of Echerer that the instant invention offers is that it does not rely on "a means for verifying the identity of said patient" or "means for establishing a mode of payment" as claimed by Echerer. Many times a patient does not have time or the desire to create an on-line identity or verify his identity before sending their vital information and receiving attention and care, let alone establishing a mode of payment. The instant invention operates without these requirements and thereby offers faster and better attention and care to a patient.

Further, the system of Echerer does not address the problem of sending, receiving, and filling necessary prescriptions for its patients.

Another apparatus, system, and method has been set forth by Sjoqvist, U.S. Pat. No. 6,409,660. This system also does include medical components that do accomplish basic telemedical functions. However, once again, there are no mechanisms, means, or methods within the Sjoqvist system that will relax a patient or better well prepare them for the reading of their vital signs. As such the readings taken may not be accurate and the medical advice and services rendered thereof may not be accurate or helpful.

Another improvement over Sjoqvist that the instant invention offers is that it does not rely on "a means for assigning priorities to different types of information upon transmission of data to a central unit" as claimed by Sjoqvist. The data receiving and interpreting mechanism on the receiving end of the instant invention retrieves and processes all the information sent by the patient in an extremely fast and efficient manner no matter how much data is sent at the same time or in what order, thereby negating the need to "prioritize" the information first and actually saving time and avoiding a degree of possible computer error.

Further, the system of Sjoqvist also does not address the problem of sending, receiving, and filling necessary prescriptions for its patients.

As for computer modules having the ability to process a patient's personal information and biological vital signs information to provide medical diagnoses, the applicant makes reference to the U.S. Pat. No. 9,224,180 of Macoviak et al, which is incorporated by reference herein, wherein its computer module(s) includes software packages that include computer algorithms encoded therein that are used to process a patient's personal information and biological vital signs information to provide medical diagnoses. Macoviak et al, however, does not provide or discuss any methods or mechanisms for relaxation integrated within their telemedical system.

As for medical components having the ability to obtain, store, and send biological vital sign information either visually or through electronic means to computer modules for processing, the applicant makes reference to the U.S. Pat. No. 8,500,636 to Tran and the U.S. Pat. No. 8,589,177 to Haq, both incorporated by reference herein, that exemplify and describe medical components having the ability to obtain, store, and send their respective biological vital sign information either visually or through electronic means to their respective computer modules for processing and providing medical diagnoses. Haq, however, does not provide or discuss any methods or mechanisms for relaxation integrated within their telemedical system.

BRIEF SUMMARY OF THE INVENTION

The instant invention is set forth as a telemedical apparatus, system, and method for providing medical services to a patient remotely using electronic communications and equipment, retrieved biological vital signs information, and personal patient information.

The "system" for providing medical services remotely includes the use of electronic communications and equipment, including but not limited to the use of internet technology, the input and interpreting of biological vital signs information and personal patient information via computer modules, and the transfer of advice and proposed medical services.

The "apparatus" for providing medical services remotely includes a primary computer module including a data input mechanism, at least one secondary computer module each including a data receiving and interpreting mechanism, electronic communication devices between the primary computer module and the at least one secondary computer module, a mechanism for relaxing a patient prior to and during use, and a mechanism for providing medical services after the patient's data and information is processed by the at least one secondary computer module, including sending, receiving, and filling necessary prescriptions for its patients.

The primary computer module incorporates advanced software packages and touch-screen capabilities. Medical components are removably connected to the primary computer module either by wires or wirelessly that perform functions such as measuring a patient's blood pressure and pulse rate, weight, cholesterol, temperature, and glucose level. These medical components may also include a spirometer for monitoring and diagnosing asthma symptoms, a diagnostic camera for up close visual inspections, including dermatological evaluations, and can be used for visual communications between a patient and a medical practitioner, and even radiological mechanisms to perform the tests and functions of a radiologist. Some of these medical components may also be attached to or even embedded within a seat, formed as a chair or recliner, or attached to a water tank that the patient may be using during the relaxation process to make it more convenient to retrieve biological vital signs from the patient once relaxed. The primary computer module is also designed to receive additional personal information and data from a patient through the data input mechanism, which includes a series of questions that the patient responds to and inputs their answers.

Before readings for the biological vital signs are taken from the patient, any one or a combination of a series of stress reducing mechanisms and techniques are used to relax the patient so that their vital signs become more steady and accurate. These mechanisms and techniques may include the use of a seat formed as a chair or recliner, handles including hand vibrators and/or hand warmers that can be attached to respective opposite vertical sides of the primary computer module, a head set that vibrates and cools a patient's head, an odorizer that produces a pleasant smell, a noise generator that plays pleasant tones or music, meditation techniques, progressive neuromuscular relaxation techniques, massage therapy, sex therapy, medicinal therapy, hypnosis, a misting mechanism, laying in a water tank, biofeedback mechanisms, virtual reality mechanisms, tickling mechanisms, reading materials, mechanisms to induce sleep, mechanisms to induce laughter, using and playing musical instruments, athletic devices, and even mechanisms for urinating and/or defecating, or any similar means, mechanisms, or methods, or combinations of any thereof.

Once the patient's personal information has been retrieved via the primary computer module data input mechanism, the patient is sufficiently relaxed via the stress reducing mechanisms and/or techniques and appropriately connected to the primary computer module via chosen medical components, their biological vital signs are retrieved. The primary computer module then connects electronically with the at least one secondary computer module, such that the patient's biological vital signs information and personal information can be sent to the at least one secondary computer module. The at least one secondary computer module can be monitored by trained personnel interfacing with the patient, and can also include computer modules with access to a large data base that includes previous patient information, a library of medical information, automated medical diagnostic tools and algorithms, and a listing of medical practitioners. Once all the necessary patient personal and vital signs information are processed by the at least one secondary computer module and a preliminary diagnosis is performed by the at least one secondary computer module, the at least one secondary computer module then provides information to the patient to help the patient connect with an appropriate medical practitioner for further diagnoses, instructions, attention, and medical services. One of the medical services that can be provided includes writing a prescription for medical treatment, wherein the prescription is forwarded electronically to the primary computer module by the at least one secondary computer module and is thereby adapted and available to be used by the patient to obtain the prescription at a pharmacy that is convenient for the patient.

Finally, the "method" for providing medical services remotely includes providing the apparatus as set forth herein, including providing a means for relaxation, providing a means for data receiving and interpreting, providing medical information and available services, and providing means for sending and filling medical prescriptions as described prior.

There has thus been outlined, rather broadly, the more important features of the invention in order that the detailed description thereof that follows may be better understood and in order that the present contribution to the art may be better appreciated.

Numerous objects, features and advantages of the present invention will be readily apparent to those of ordinary skill in the art upon a reading of the following detailed description of presently preferred, but nonetheless illustrative, embodiments of the present invention when taken in conjunction with the accompanying drawings. The invention is capable of other embodiments and of being practiced and carried out in various ways. Also, it is to be understood that the phraseology and terminology employed herein are for the purpose of descriptions and should not be regarded as limiting.

BRIEF DESCRIPTION OF THE DRAWINGS

The figures which accompany the written portion of this specification illustrate embodiments according to the teachings of the present invention.

DETAILED DESCRIPTION

The embodiments of the present disclosure described below are not intended to be exhaustive or to limit the disclosure to the precise forms disclosed in the following detailed description. Rather, the embodiments are chosen and described so that others skilled in the art may appreciate and understand the principles and practices of the present disclosure.

The following embodiments and the accompanying drawings, which are incorporated into and form part of this disclosure, illustrate embodiments of the invention and together with the description, serve to explain the principles of the invention. To the accomplishment of the foregoing and related ends, certain illustrative aspects of the invention are described herein in connection with the following description and the annexed drawings. These aspects are indicative, however, of but a few of the various ways in which the principles of the invention can be employed and the subject invention is intended to include all such aspects and their equivalents. Other advantages and novel features of the invention will become apparent from the following detailed description of the invention when considered in conjunction with the drawings.

The preferred embodiment of the instant invention is illustrated in FIGS. 1-8 as a telemedical apparatus, system, and method for diagnosing and treating a patient remotely.

Figure 1:
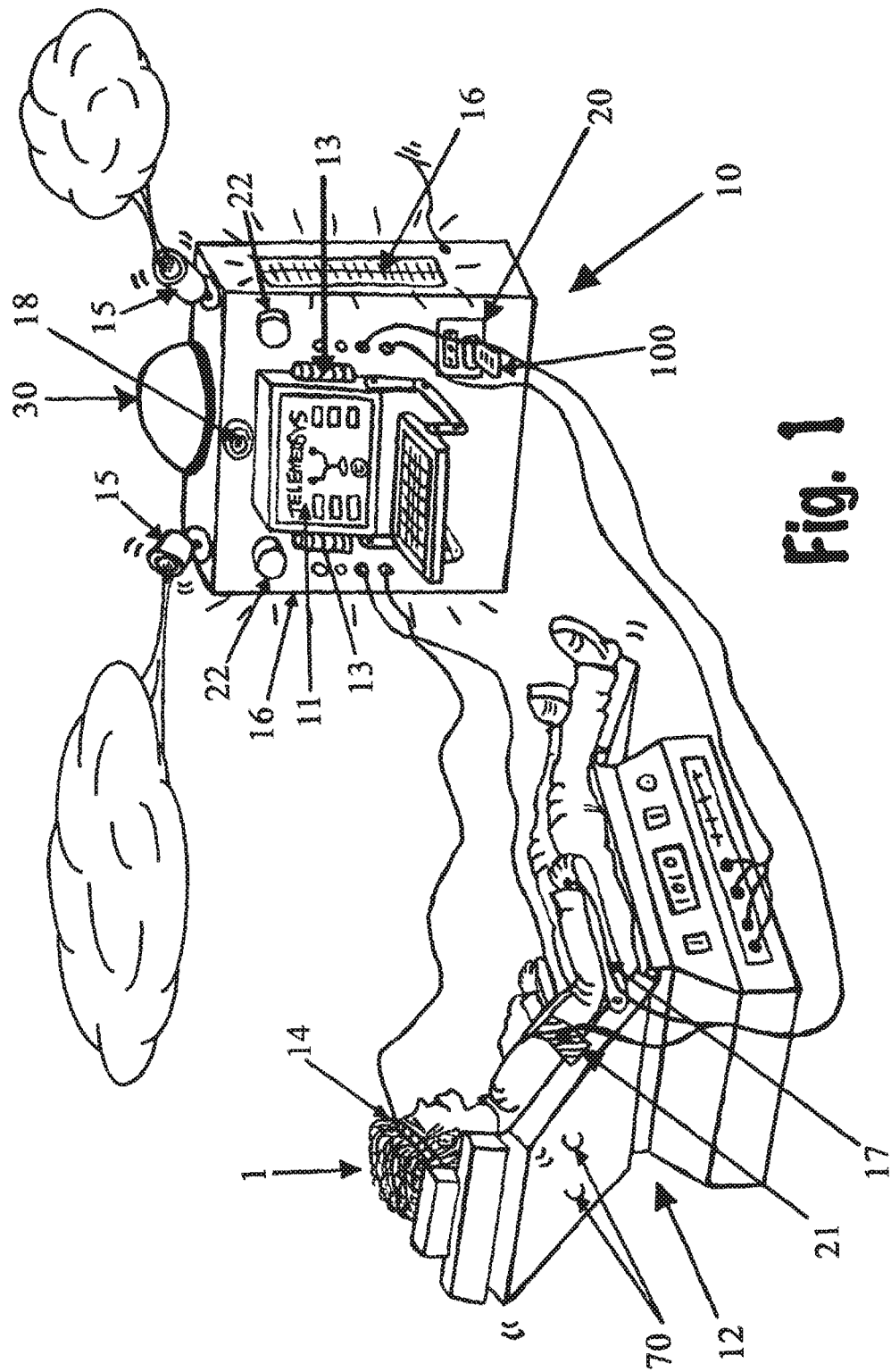
FIG. 1 is a perspective view of the telemedical apparatus including the primary computer module, the data input mechanism, mechanisms for relaxation, medical components to retrieve biological vital signs, and the mechanism for receiving and printing prescriptions.
Figure 2:
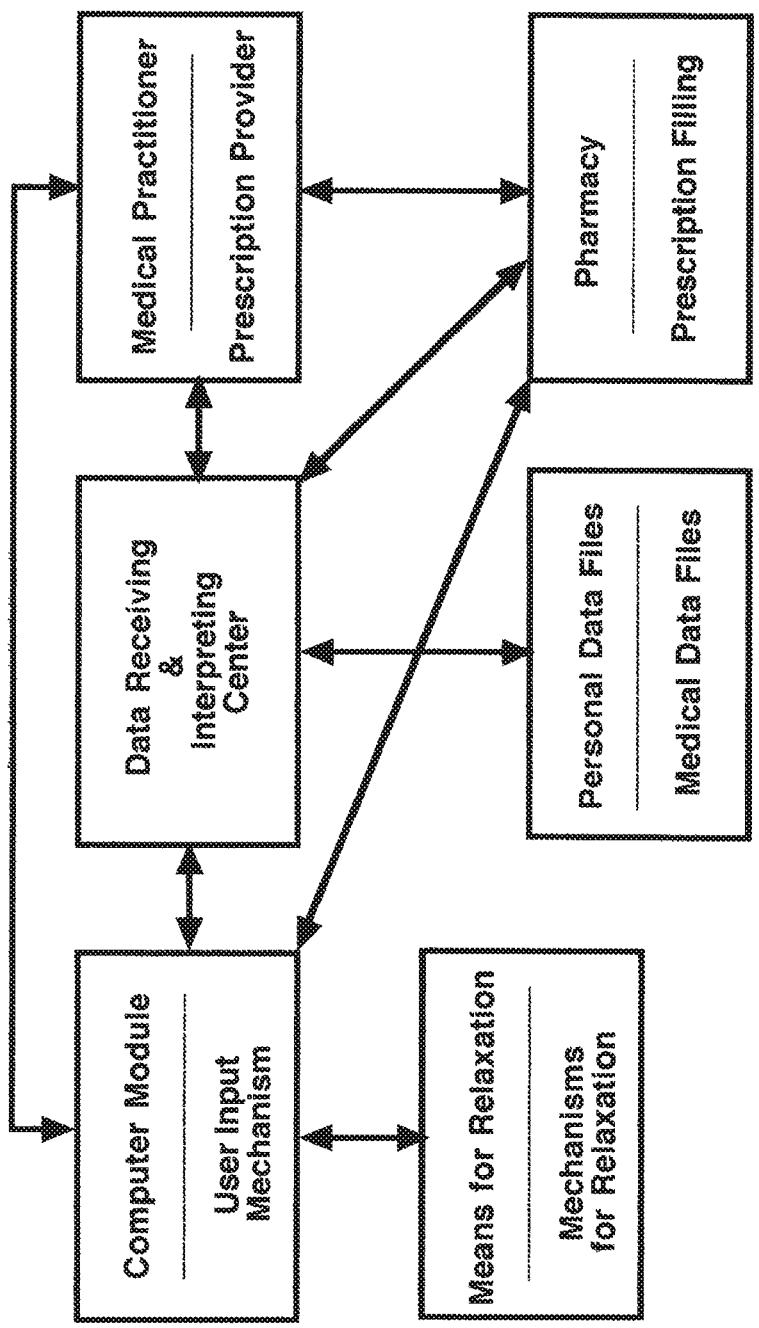
FIG. 2 is a flow chart showing the preferred interrelationships between portions of the telemedical system and method.

FIG. 1 illustrates a perspective view of the telemedical apparatus including the primary computer module 10, mechanisms for relaxation described in further detail below, medical components, including a mechanism to measure and record blood pressure and pulse rate 21 contacting a patient, and the mechanism for receiving and printing prescriptions 20. The primary computer module 10 incorporates many of the modern technical equipment, including advanced software packages and touch-screen technology.

An electronic communication mechanism, including member 30, is also provided and adapted to be connected to the primary computer module 10 and includes wireless internet sending and receiving mechanisms adapted to electronically connect the primary computer module to at least one remotely located secondary computer module, such that the primary computer module 10 is adapted to collect a patient's personal information and biological vital signs information, send the patient's personal information and said biological vital signs information electronically to a secondary computer module, receive diagnosing and treatment information from the secondary computer module, and provide the diagnosing and treatment information to said patient.

When a patient 1 first approaches the telemedical system primary computer module they simply touch the primary computer module screen 11 where it displays the instruction to do so, such as a "Press here to begin" image. The patient will then be greeted by voice and/or visual commands to guide them through a process that includes the input of that patient's necessary personal and biological vital sign information using the primary computer module touch screen capabilities or optional keyboard and selected vital sign retrieving medical components, described in further detail below.

Figure 3:
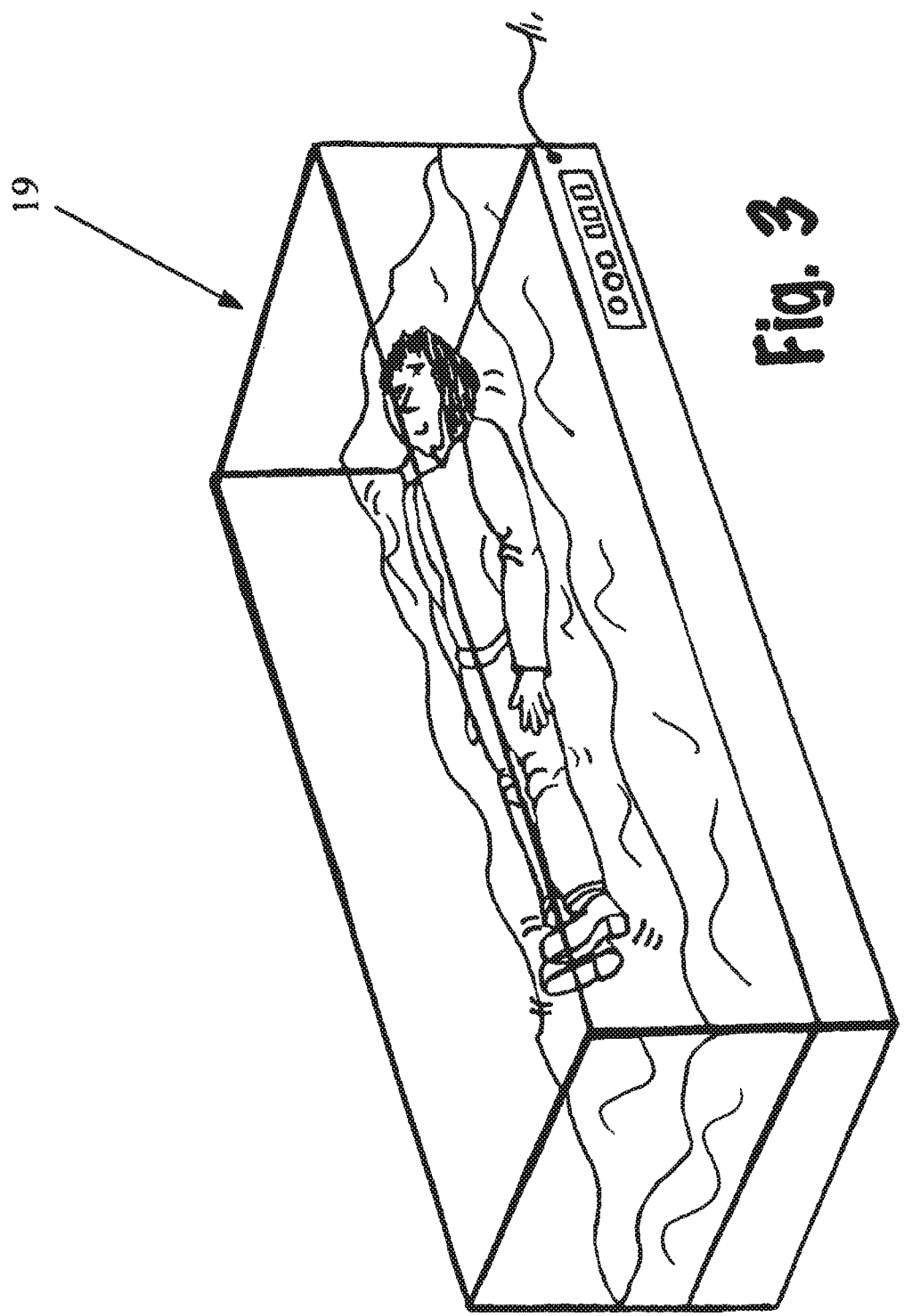
FIG. 3 is a perspective view of a water tank being used as the mechanism for relaxation.

Once the patient is logged in and ready they can choose between any one or a combination of a series of the stress reducing means and mechanisms and techniques offered and used to relax the patient so that their biological vital signs become more steady/stable and accurate. These means, mechanisms, and techniques may include the use of a seat 12 formed as a chair or recliner that may include a foot rest pivotably attached thereto and a head rest pivotably attached to a back rest thereof; handles 13 including hand vibrators and hand warmers that can be releasably attached to each respective opposite vertical side of the primary computer module screen or casing; a head set 14 that vibrates and cools a patient's head; odorizing and misting members 15 that produces pleasant smells and mist; noise generators 16 that plays pleasant tones or music; meditation techniques; progressive neuromuscular relaxation techniques; massage therapy which can be accomplished by incorporating vibrators into seat 12 to vibrate seat 12, and incorporating rollers 70 therein; medicinal therapy 17, which can be in the form of a tube adapted to transfer medicine from the primary computer 10 to the patient; mechanisms for sex therapy; hypnosis, which can be accomplished using mechanism 18 that spins in a hypnotic pattern wherein the patient can watch and concentrate on mechanism 18 and become hypnotized and relaxed; a water tank 19, as shown in FIG. 3, for a patient to lay and float in; biofeedback mechanisms; virtual reality mechanisms; tickling mechanisms; reading materials; mechanisms to induce sleep; mechanisms to induce laughter; using and playing musical instruments; using athletics devices; and even mechanisms for urinating and/or defecating; and any similar means, mechanisms, or methods, or combinations thereof.

Figure 7:
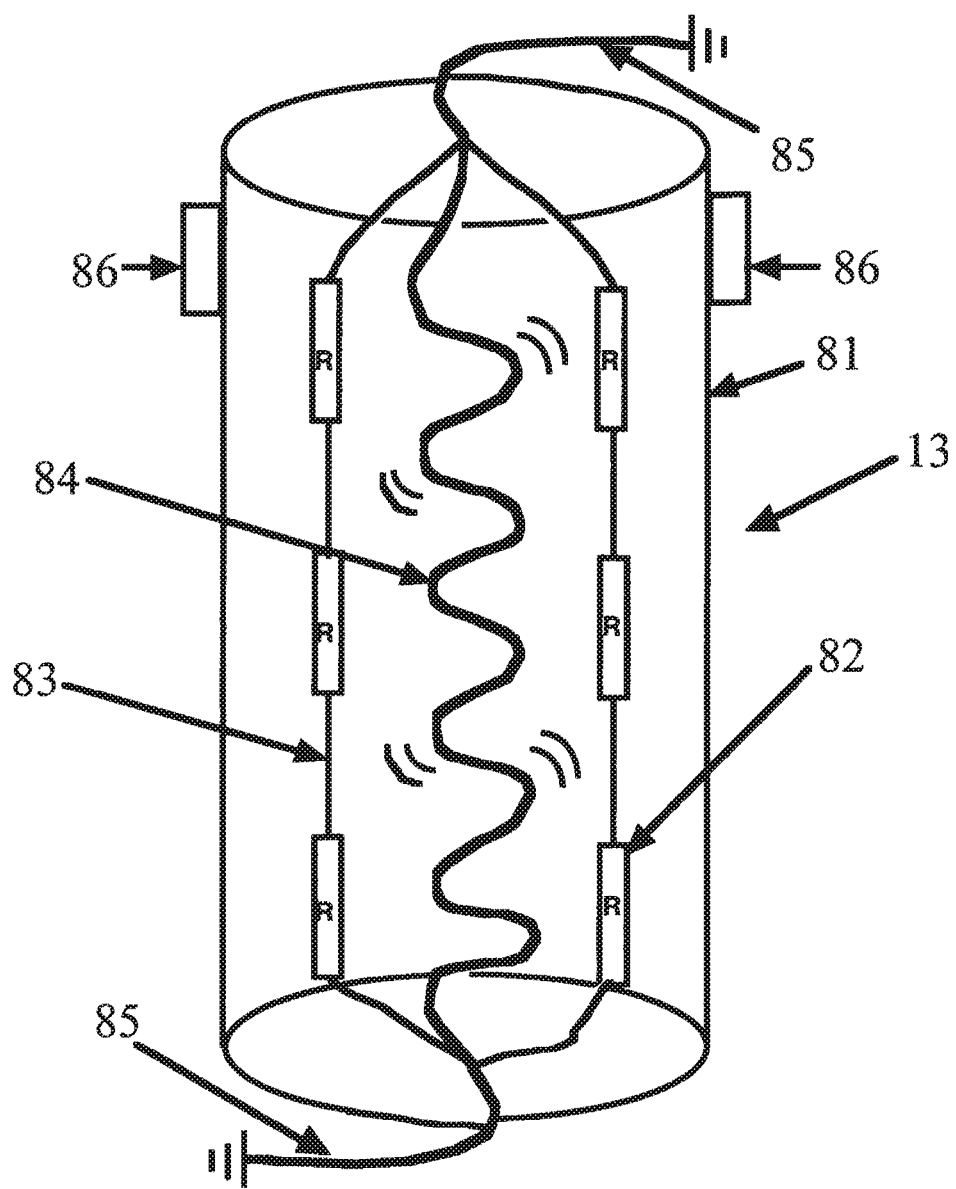
FIG. 7 is a perspective view of the means for relaxation formed as handles including hand warmers and hand vibrators.

A more detailed illustration of the handles 13 including hand vibrators and hand warmers is set forth in FIG. 7. In this embodiment the handles 13 are formed having hollow cylindrical bodies 81. Within and attached to the inner walls of the cylindrical bodies are resistor members 82, which are individually marked each with an R and are interconnected by electric wires 83, that heat up when a current is passed therethrough via main electric wire 85. Further, a vibrating member 84, which in this embodiment is formed as a spring type member, passes through the middle of the body and vibrates when the current is passed therethrough via main electric wire 85. The handles 13 are electrically connected to the primary computer module via the electric conductor members 85, and releasably mechanically connected to the primary computer module via connector members 86. When the patient chooses this means for relaxation, they place one hand on each handle 13. The primary computer module then sends an electric current through main electric wire 85 and electric wires 83 to heat and vibrate the patient's hands until the patient is sufficiently relaxed.

Figure 8:
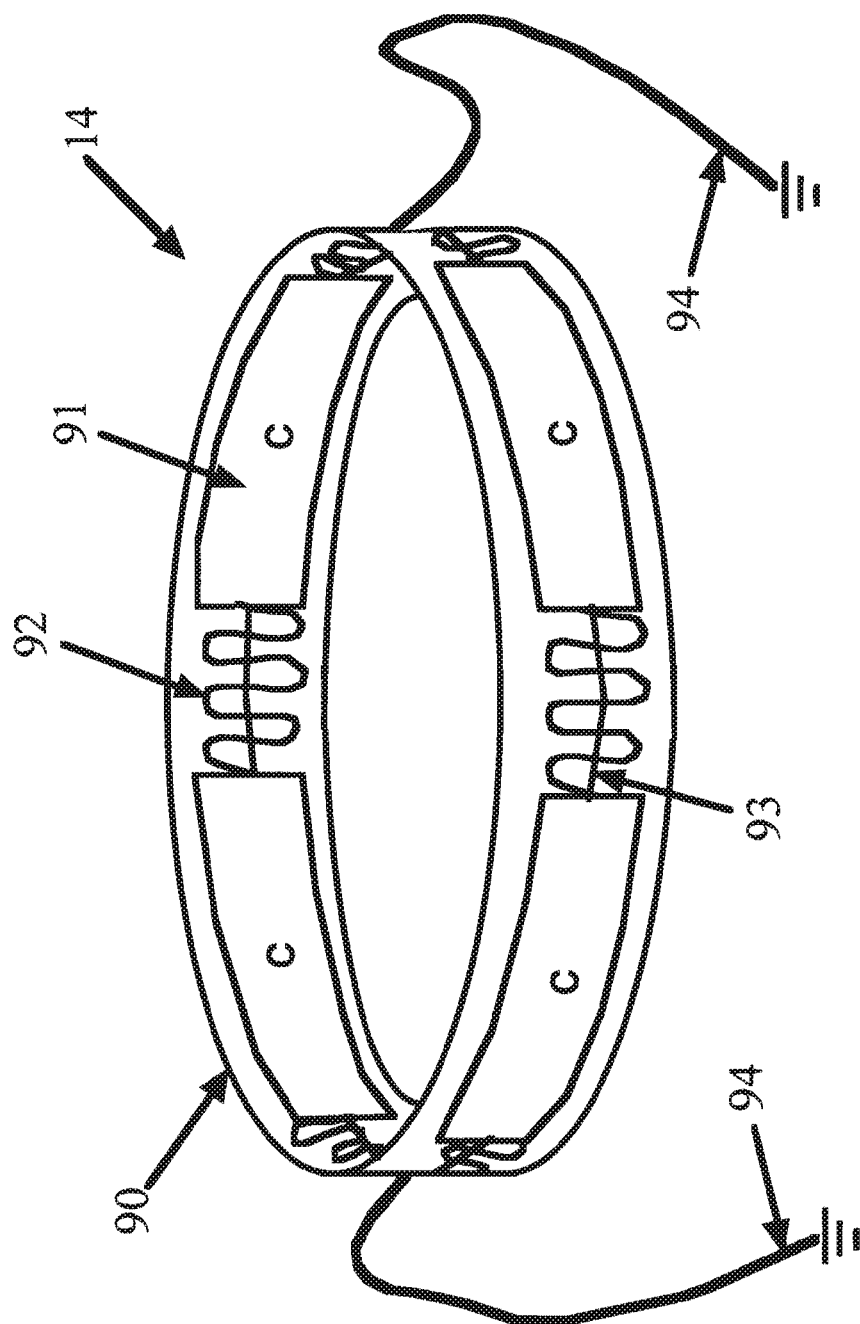
FIG. 8 is a perspective view of the means for relaxation formed as a head set that vibrates and cools a patient's head.

A more detailed illustration of the head set 14 that vibrates and cools a patient's head is set forth in FIG. 8. In this embodiment the head set is formed as a circular band 90 having condenser cooling members 91 interconnected by electrical wires 93, and vibrator members 92 interconnected between the condenser cooling members and attached to the inner side thereof. The condenser cooling members and vibrators are electrically connected to the primary computer module via main electric wire 94. When the patient chooses this means for relaxation, they place the head set on their head. The primary computer module then send an electric current through the electric wires 93 and main electric wire 94 to the cooling and vibrating members until the patient is sufficiently relaxed.

A meditation technique, a progressive neuromuscular relaxation technique, and a hypnosis technique are also being employed and used by patient 1 and illustrated in FIG. 1. As such, the patient can meditate by concentrating on odorizing and misting members 15 that produces pleasant smells and mist, noise generators 16 that plays pleasant tones or music, and mechanism 18 that spins with a hypnotic pattern. As a result, patient 1 is in a sufficiently relaxed state for their biological vital signs to be taken.

Once the patient is ready for biological vital sign entry, biological vital sign retrieving medical components are connected to the patient, including in no particular order, mechanisms to measure and record blood pressure and pulse rate (for example, member 21 shown in FIG. 1 attached to the reclining back rest member of the seat and electronically connected to the primary computer module 10), weight, cholesterol, temperature, and glucose level. These medical components can also include a spirometer for monitoring and diagnosing asthma symptoms; three-dimensional diagnostic cameras (for example, members 22 shown in FIG. 1) for up close visual inspections, including dermatological evaluations, and can be used for visual communications between a patient and a medical practitioner; and even radiological mechanisms. These medical components may also be attached to or even embedded within a seat, formed as a chair or recliner, or attached to a water tank that the patient may be using during the relaxation process to make it more convenient to retrieve biological vital signs from the patient once relaxed. Each medical component is also adapted to be electronically connected to the primary computer module 10 wherein the biological vital sign information collected is then transferred electronically to the computer module 10. The computer module 10 is adapted to control each medical component using advanced computer software and algorithms encoded thereon, and to control the transfer of biological vital signs from each respective medical component thereto.

Figure 4:
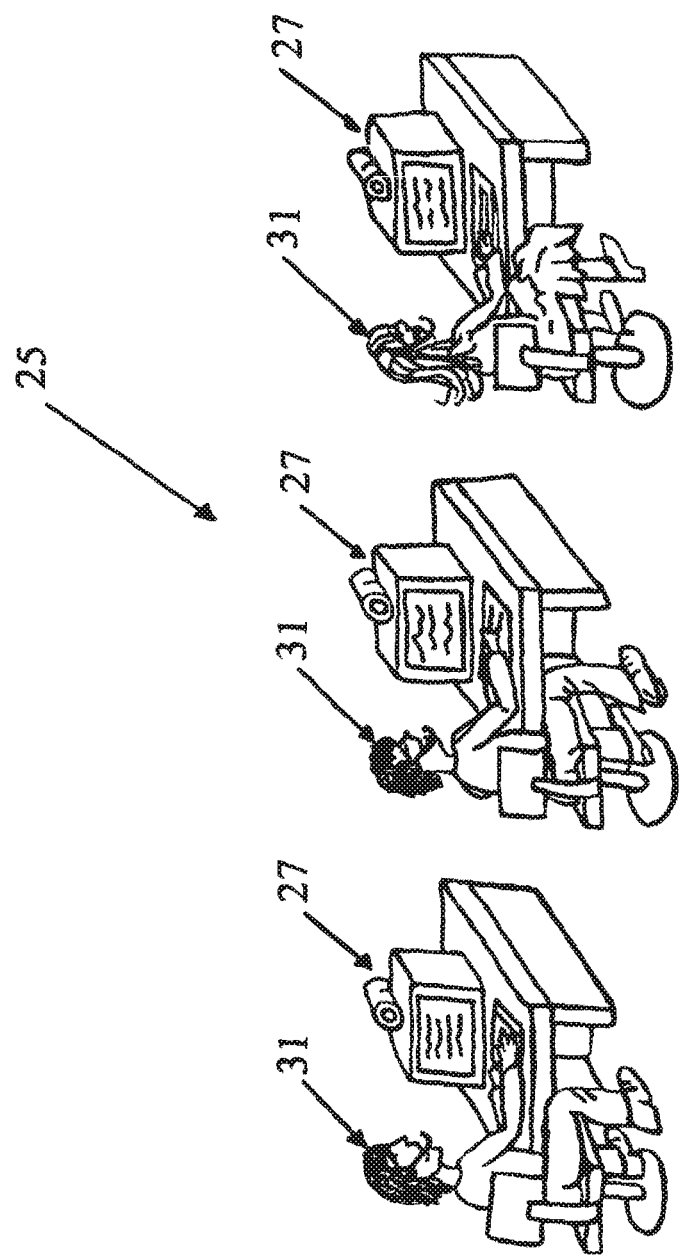
FIG. 4 is a perspective view of a plurality of secondary computers being monitored by trained personnel.

Once the patient properly connects to the primary computer module 10 and their biological vital signs information and necessary personal information have been entered therein, the primary computer module 10 connects electronically, via electronic communication mechanism 30 and available internet resources, with a remotely located call center 25, as illustrated in FIG. 4, and sends the patient's personal information and biological vital signs information to one of a plurality of secondary computer modules 27. The call center 25 may include trained personnel 31 available to interface with the patient if necessary, and does include a plurality of secondary computer modules 27 that have access to large data bases that includes prior patient information, a library of medical information, automated medical diagnostic tools and algorithms, and a listing of medical practitioners. Each of the plurality of secondary computer modules 27 further include advanced software packages that include algorithms encoded therein adapted to generate medical diagnoses, and which operate with similar steps and procedures as the software and algorithms of Macoviak et al 9,224,180, which is incorporated by reference herein.

Figure 5:
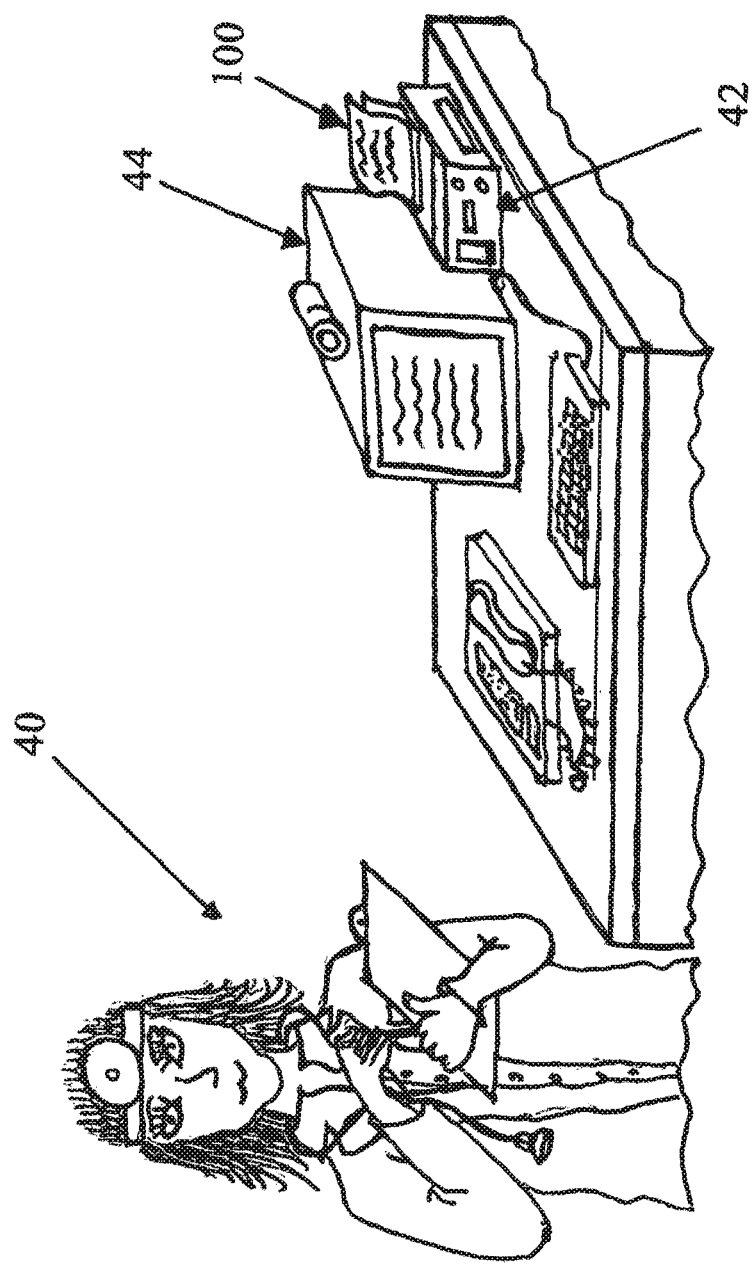
FIG. 5 is a view of a remotely located medical practitioner monitoring a mechanism for sending prescriptions electronically.

Once all of the patient's personal information, prior patient information, and biological vital signs information are collected by and processed by the secondary computer module 27 via its software packages and algorithms encoded therein, a diagnosis is generated and treatment information is compiled by the secondary computer module 27. The secondary computer module 27 then sends the diagnosis and treatment information to the primary computer module 10 via the electronic communication mechanism, including member 30, and available internet resources, to thereby enable the patient to connect with an appropriate medical practitioner 40, as illustrated in FIG. 5, for further instructions, attention, and suggested medical services. The medical practitioner also has the ability and means to research, diagnose, and write and send prescriptions to either the patient directly via the electronic communication mechanism, including member 30, or through the secondary computer module 27. As shown in FIG. 5, medical practitioner 40 can use a scanning and/or facsimile device 42 to retrieve and send prescriptions, or create a computer file and send prescriptions using prescription software, computer module 44, and internet technology, or any variation or combination of known technologies.

Figure 6:
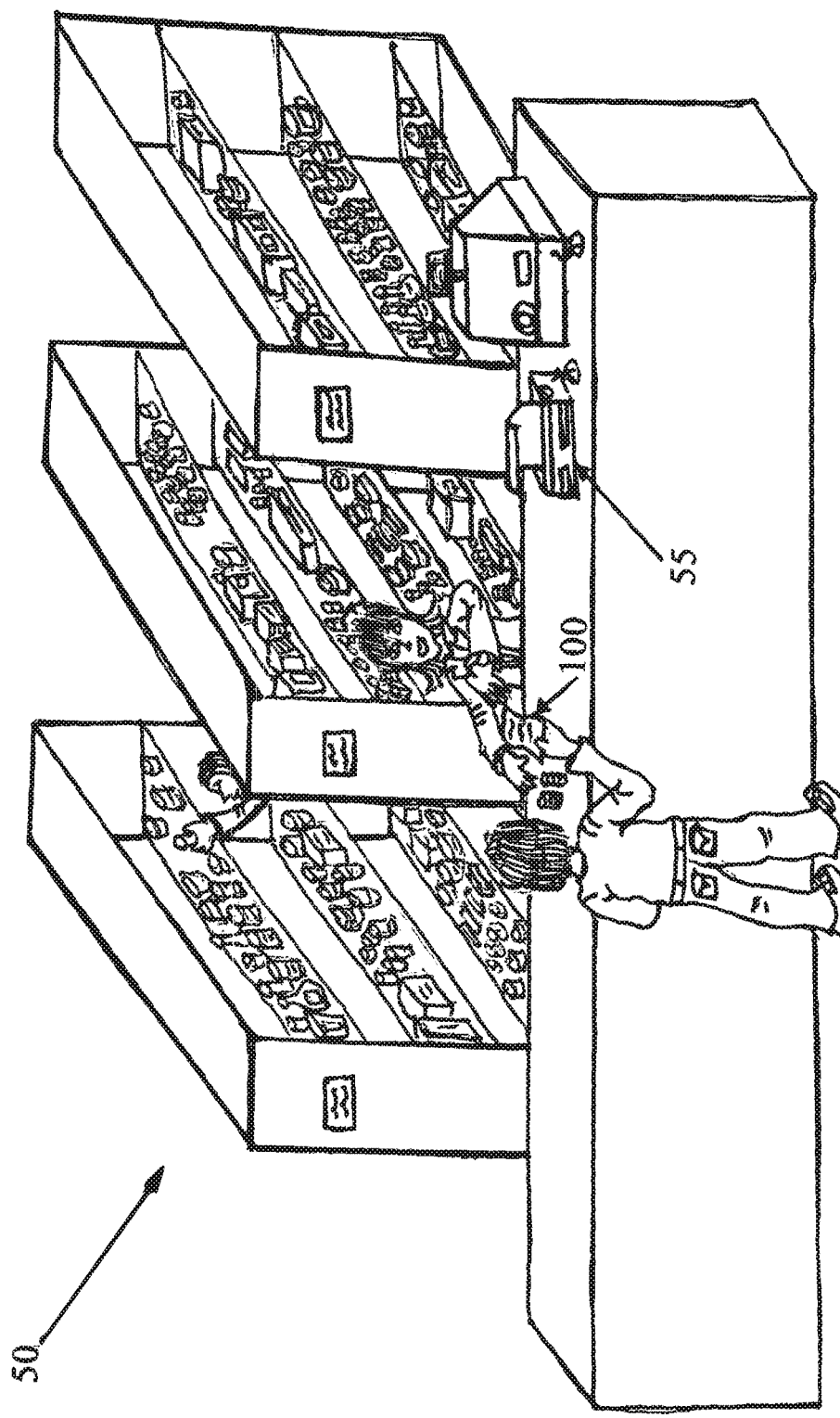
FIG. 6 is a perspective view of a patient visiting a pharmacy to have their prescription filled.

One of the most important medical services provided within this apparatus, system, and method of providing medical services remotely includes providing a mechanism for receiving and printing a prescription, illustrated in FIG. 1 as member 20. The prescription, viewed in FIGS. 1, 5, and 6 as member 100, can then be carried by the patient to a convenient pharmacy 50 to fill, as illustrated in FIG. 6. The mechanism for receiving and printing a prescription can be formed as a combination of facsimile software within the primary computer module and a small printing mechanism 20 communicating with the primary computer module. The mechanism for receiving and printing a prescription can be also formed as digital files created by a medical professional and sent electronically to the primary computer module to be stored or printed. Or any equivalent or obvious variations thereof. Therefore, a prescription can be written by a medical professional, sent electronically to the primary computer module, printed by the printing mechanism, obtained by the patient, taken by the patient to a convenient and local pharmacy, and filled by said pharmacy.

A variation of the mechanism for receiving and printing a prescription would be to have a chosen pharmacy 50 adapted and capable of receiving the patient's prescription directly, either using computer files or facsimile technology and a printer, for example, member 55 in FIG. 6. The patient could then either pick up the prescription in person or have the prescription delivered to a chosen location.

Although specific embodiments have been illustrated and described herein, it will be appreciated by those of ordinary skill in the art that any arrangement, which is calculated to achieve the same purpose, may be substituted for the specific embodiment shown. This application is intended to cover any adaptations or variations of the present invention.

Although the invention has been explained in relation to its preferred embodiment, it is to be understood that many other possible modifications and variations can be made without departing from the spirit and scope of the invention.

What is claimed is:

1. A method for providing telemedical services for diagnosing and treating a patient remotely, comprising the steps of:
    providing a primary computer module including:
        a data input mechanism;
            wherein said data input mechanism is adapted to allow a patient to input personal information into said primary computer module;
        wherein said primary computer module is adapted to collect said patient's personal information and biological vital signs information of said patient, send said patient's personal information and said patient's biological vital signs information of electronically to a secondary computer module, receive diagnosing and treatment information from said secondary computer module, and provide said diagnosing and treatment information to said patient;
    providing said secondary computer module:
        wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;
    providing an electronic communication mechanism;
        wherein said electronic communication mechanism is adapted to be electronically connected between and communicate with said primary computer module and said secondary computer module, to thereby send said patient's personal information and said patient's biological vital signs information electronically from said primary computer module to said secondary computer module, and
        electronically send said diagnosing and treatment information back to said primary computer module;
    providing mechanisms for relaxation including:
        a seat; and a reclining back rest pivotably attached to said seat;
        wherein said seat and said reclining back rest are adapted to be connected with said primary computer module and are adapted to stabilize biological vital signs of said patient before said patient's biological vital signs information is collected and sent by said primary computer module; and at least one handle that includes at least one hand vibrator and at least one hand warmer; wherein each of said at least one handle are adapted to be mechanically and electrically attached to said primary computer module and further stabilize said biological vital signs before said patient's biological vital signs information is collected and sent by said primary computer module;
    providing at least one medical component;
        wherein each of said at least one medical component is adapted to be releasably connected to said primary computer module; and
        wherein each of said at least one medical component is adapted to obtain and send said patient's biological vital signs information to said primary computer module;
    using said data input mechanism of said primary computer module to collect said personal information of said patient;
    using said mechanisms for relaxation to stabilize said patient's biological vital signs;
    using each of said at least one medical component to obtain and send said patient's biological vital signs information to said primary computer module after using said mechanisms for relaxation to stabilize said patient's biological vital signs;
    using said primary computer module to collect said patient's biological vital signs information from each of said at least one medical component after using said mechanisms for relaxation to stabilize said patient's biological vital signs, and sending said patient's personal information and said patient's biological vital signs information to said secondary computer module via said electronic communication mechanism; and using said secondary computer module to receive and process said patient's personal information and said patient's biological vital signs information, retrieve said available prior personal information of said patient, and compile and send said diagnosing and treatment information back to said primary computer module via said electronic communication mechanism for said patient to retrieve and use.

2. The method for providing telemedical services of claim 1, further comprising the step of providing and connecting a mechanism for receiving and printing medical prescriptions to said primary computer module.

3. The method for providing telemedical services of claim 1, wherein said electronic communication mechanism includes communication technology adapted to make use of internet, radio, telephony, teletype, and facsimile technologies.

4. The method for providing telemedical services of claim 1, wherein said data input mechanism of said primary computer module comprises a keyboard.

5. The method for providing telemedical services of claim 1, wherein said data input mechanism of said primary computer module includes a primary computer module screen incorporating touch-screen technology adapted to allow said patient to input information into said primary computer module.

6. The method for providing telemedical services of claim 1, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

7. The method for providing telemedical services of claim 1, wherein said mechanisms for relaxation further include a foot rest pivotably attached to said seat; and a head rest pivotably attached to said back rest.

8. A method for providing telemedical services for diagnosing and treating a patient remotely, comprising the steps of:
providing a primary computer module including:
a data input mechanism;
wherein said data input mechanism is adapted to allow a patient to input personal information into said primary computer module;
wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;
providing said secondary computer module:
wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;
providing an electronic communication mechanism;
wherein said electronic communication mechanism is adapted to be electronically connected between and communicate with said primary computer module and said secondary computer module, to thereby send said patient's personal information and said patient's biological vital signs information electronically from said primary computer module to said secondary computer module, and electronically send said diagnosing and treatment information back to said primary computer module;
providing a mechanism for relaxation;
wherein said mechanism for relaxation comprises at least one handle that includes at least one hand vibrator and at least one hand warmer;
wherein each of said at least one handle are adapted to be mechanically and electrically attached to said primary computer module; and
wherein said mechanism for relaxation is adapted to be connected with said primary computer module and is adapted to stabilize biological vital signs of said patient before said patient's biological vital signs information is collected and sent by said primary computer module;
providing at least one medical component;
wherein each of said at least one medical component is adapted to be releasably connected to said primary computer module; and
wherein each of said at least one medical component is adapted to obtain and send said patient's biological vital signs information to said primary computer module;
using said data input mechanism of said primary computer module to collect said personal information of said patient;
using said mechanism for relaxation to stabilize said patient's biological vital signs;
using each of said at least one medical component to obtain and send said patient's biological vital signs information to said primary computer module after using said mechanism for relaxation to stabilize said patient's biological vital signs;
using said primary computer module to collect said patient's biological vital signs information from each of said at least one medical component after using said mechanism for relaxation to stabilize said patient's biological vital signs, and sending said patient's personal information and said patient's biological vital signs information to said secondary computer module via said electronic communication mechanism; and
using said secondary computer module to receive and process said patient's personal information and said patient's biological vital signs information, retrieve said available prior personal information of said patient, and compile and send said diagnosing and treatment information back to said primary computer module via said electronic communication mechanism for said patient to retrieve and use.

9. The method for providing telemedical services of claim 8, wherein said data input mechanism of said primary computer module includes a primary computer module screen incorporating touch-screen technology adapted to allow said patient to input information into said primary computer module.

10. The method for providing telemedical services of claim 8, further comprising the step of providing and connecting a mechanism for receiving and printing medical prescriptions to said primary computer module.

11. The method for providing telemedical services of claim 8, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

12. A method for providing telemedical services for diagnosing and treating a patient remotely, comprising the steps of:
  providing a primary computer module including:
    a data input mechanism;
      wherein said data input mechanism is adapted to allow a patient to input personal information into said primary computer module;
    wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;
  providing said secondary computer module:
    wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;
  providing an electronic communication mechanism;
    wherein said electronic communication mechanism is adapted to be electronically connected between and communicate with said primary computer module and said secondary computer module, to
      thereby send said patient's personal information and said patient's biological vital signs information electronically from said primary computer module to said secondary computer module, and
      electronically send said diagnosing and treatment information back to said primary computer module;
  providing a mechanism for relaxation;
    wherein said mechanism for relaxation comprises a head set adapted to be electrically connected to said primary computer module, wherein said head set includes vibrators and cooling elements adapted to be placed on said patient's head for vibrating and cooling said patient's head; and
    wherein said mechanism for relaxation is adapted to be connected with said primary computer module and is adapted to stabilize biological vital signs of said patient before said patient's biological vital signs information is collected and sent by said primary computer module;
  providing at least one medical component;
    wherein each of said at least one medical component is adapted to be releasably connected to said primary computer module; and
    wherein each of said at least one medical component is adapted to obtain and send said patient's biological vital signs information to said primary computer module;
  using said data input mechanism of said primary computer module to collect said personal information of said patient;
  using said mechanism for relaxation to stabilize said patient's biological vital signs;
  using each of said at least one medical component to obtain and send said patient's biological vital signs information to said primary computer module after using said mechanism for relaxation to stabilize said patient's biological vital signs;
  using said primary computer module to collect said patient's biological vital signs information from each of said at least one medical component after using said mechanism for relaxation to stabilize said patient's biological vital signs, and sending said patient's personal information and said patient's biological vital signs information to said secondary computer module via said electronic communication mechanism; and
  using said secondary computer module to receive and process said patient's personal information and said patient's biological vital signs information, retrieve said available prior personal information of said patient, and compile and send said diagnosing and treatment information back to said primary computer module via said electronic communication mechanism for said patient to retrieve and use.

13. The method for providing telemedical services of claim 12, wherein said data input mechanism of said primary computer module includes a primary computer module screen incorporating touch-screen technology adapted to allow said patient to input information into said primary computer module.

14. The method for providing telemedical services of claim 12, wherein said head set further includes a circular head band; wherein said vibrators and cooling elements are attached to an inner side of said circular head band, are interconnected by electric wires, and are electrically connected to said primary computer module via a main electric wire, such that when an electric current is passed therethrough via said main electric wire said cooling elements reduce in temperature and said vibrators vibrate.

15. The method for providing telemedical services of claim 12, further comprising the step of providing and connecting a mechanism for receiving and printing medical prescriptions to said primary computer module.

16. In an apparatus for providing telemedical services for diagnosing and treating a patient remotely comprising:
  a primary computer module including:
    a data input mechanism;
      wherein said data input mechanism is adapted to allow a patient to input personal information into said primary computer module;
    wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;

said secondary computer module:
  wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;

an electronic communication mechanism;
  wherein said electronic communication mechanism is adapted to be electronically connected between and communicate with said primary computer module and said secondary computer module, to
  thereby send said patient's personal information and said patient's biological vital signs information electronically from said primary computer module to said secondary computer module, and
  electronically send said diagnosing and treatment information back to said primary computer module; and at least one medical component;
  wherein each of said at least one medical component is adapted to be releasably connected to said primary computer module; and
  wherein each of said at least one medical component is adapted to obtain and send said patient's biological vital signs information to said primary computer module;

the improvement comprising mechanisms for relaxation including:
  a seat; and a reclining back rest pivotably attached to said seat;
  wherein said seat and said reclining back rest are adapted to be connected with said primary computer module and are adapted to stabilize biological vital signs of said patient before said patient's biological vital signs information is collected and sent by said primary computer module; and at least one handle that includes at least one hand vibrator and at least one hand warmer; wherein each of said at least one handle are adapted to be mechanically and electrically attached to said primary computer module and further stabilize said biological vital signs before said patient's biological vital signs information is collected and sent by said primary computer module;

wherein said data input mechanism of said primary computer module is used to collect said personal information of said patient;

wherein said mechanisms for relaxation are used to stabilize said patient's biological vital signs;

wherein each of said at least one medical component is used to obtain and send said patient's biological vital signs information to said primary computer module after using said mechanisms for relaxation to stabilize said patient's biological vital signs;

wherein said primary computer module is used to collect said patient's biological vital signs information from each of said at least one medical component after using said mechanisms for relaxation to stabilize said patient's biological vital signs, and send said patient's personal information and said patient's biological vital signs information to said secondary computer module via said electronic communication mechanism; and wherein said secondary computer module is used to receive and process said patient's personal information and said patient's biological vital signs information, retrieve said available prior personal information of said patient, and compile and send said diagnosing and treatment information back to said primary computer module via said electronic communication mechanism for said patient to retrieve and use.

17. The apparatus of claim 16, wherein the improvement further comprises a mechanism for receiving and printing medical prescriptions adapted to be connected to said primary computer module.

18. The apparatus of claim 16, wherein said mechanisms for relaxation further comprise a foot rest pivotably attached to said seat; and a head rest pivotably attached to said back rest.

19. The apparatus of claim 16, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

20. In an apparatus for providing telemedical services for diagnosing and treating a patient remotely comprising:
  a primary computer module including:
    a data input mechanism;
      wherein said data input mechanism is adapted to allow a patient to input personal information into said primary computer module;
    wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;
  said secondary computer module:
    wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;
  an electronic communication mechanism;
    wherein said electronic communication mechanism is adapted to be electronically connected between and communicate with said primary computer module and said secondary computer module, to
    thereby send said patient's personal information and said patient's biological vital signs information electronically from said primary computer module to said secondary computer module, and electronically send said diagnosing and treatment information back to said primary computer module; and at least one medical component;

wherein each of said at least one medical component is adapted to be releasably connected to said primary computer module; and wherein each of said at least one medical component is adapted to obtain and send said patient's biological vital signs information to said primary computer module;

the improvement comprising a mechanism for relaxation;

wherein said mechanism for relaxation comprises at least one handle that includes at least one hand vibrator and at least one hand warmer;

wherein each of said at least one handle are adapted to be mechanically and electrically attached to said primary computer module; and wherein said mechanism for relaxation is adapted to be connected with said primary computer module and is adapted to stabilize biological vital signs of said patient before said patient's biological vital signs information is collected and sent by said primary computer module;

wherein said data input mechanism of said primary computer module is used to collect said personal information of said patient;

wherein said mechanism for relaxation is used to stabilize said patient's biological vital signs;

wherein each of said at least one medical component is used to obtain and send said patient's biological vital signs information to said primary computer module after using said mechanism for relaxation to stabilize said patient's biological vital signs;

wherein said primary computer module is used to collect said patient's biological vital signs information from each of said at least one medical component after using said mechanism for relaxation to stabilize said patient's biological vital signs, and send said patient's personal information and said patient's biological vital signs information to said secondary computer module via said electronic communication mechanism; and wherein said secondary computer module is used to receive and process said patient's personal information and said patient's biological vital signs information, retrieve said available prior personal information of said patient, and compile and send said diagnosing and treatment information back to said primary computer module via said electronic communication mechanism for said patient to retrieve and use.

21. The apparatus of claim 20, wherein the improvement further comprises a mechanism for receiving and printing medical prescriptions adapted to be connected to said primary computer module.

22. The apparatus of claim 20, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

23. In an apparatus for providing telemedical services for diagnosing and treating a patient remotely comprising:

a primary computer module including:

a data input mechanism;

wherein said data input mechanism is adapted to allow a patient to input personal information into said primary computer module;

wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;

said secondary computer module:

wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;

an electronic communication mechanism;

wherein said electronic communication mechanism is adapted to be electronically connected between and communicate with said primary computer module and said secondary computer module, to thereby send said patient's personal information and said patient's biological vital signs information electronically from said primary computer module to said secondary computer module, and electronically send said diagnosing and treatment information back to said primary computer module; and at least one medical component;

wherein each of said at least one medical component is adapted to be releasably connected to said primary computer module; and wherein each of said at least one medical component is adapted to obtain and send said patient's biological vital signs information to said primary computer module;

the improvement comprising a mechanism for relaxation;

wherein said mechanism for relaxation comprises a head set adapted to be electrically connected to said primary computer module, wherein said head set includes vibrators and cooling elements adapted to be placed on said patient's head for vibrating and cooling said patient's head; and wherein said mechanism for relaxation is adapted to be connected with said primary computer module and is adapted to stabilize biological vital signs of said patient before said patient's biological vital signs information is collected and sent by said primary computer module;

wherein said data input mechanism of said primary computer module is used to collect said personal information of said patient;

wherein said mechanism for relaxation is used to stabilize said patient's biological vital signs;

wherein each of said at least one medical component is used to obtain and send said patient's biological vital signs information to said primary computer module after using said mechanism for relaxation to stabilize said patient's biological vital signs;

wherein said primary computer module is used to collect said patient's biological vital signs information from each of said at least one medical component after using said mechanism for relaxation to stabilize said patient's biological vital signs, and send said patient's personal information and said patient's biological vital signs information to said secondary computer module via said electronic communication mechanism; and wherein said secondary computer module is used to receive and process said patient's personal information and said patient's biological vital signs information, retrieve said available prior personal information of said patient, and compile and send said diagnosing and treatment information back to said primary computer module via said electronic communication mechanism for said patient to retrieve and use.

24. The apparatus of claim 23, wherein the improvement further comprises a mechanism for receiving and printing medical prescriptions adapted to be connected to said primary computer module.

25. The apparatus of claim 23, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

26. A method for providing telemedical services for diagnosing and treating a patient remotely, comprising the steps of:

providing a primary computer module including:
a data input mechanism;
wherein said data input mechanism is adapted to allow a patient to input personal information into said primary computer module;
wherein said primary computer module is adapted to collect said patient's personal information and biological vital signs information, send said patient's personal information and said patient's biological vital signs information electronically to a secondary computer module, receive diagnosing and treatment information from said secondary computer module, and provide said diagnosing and treatment information to said patient;

providing said secondary computer module:
wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;

providing an electronic communication mechanism;
wherein said electronic communication mechanism is adapted to be electronically connected between and communicate with said primary computer module and said secondary computer module, to thereby send said patient's personal information and said patient's biological vital signs information electronically from said primary computer module to said secondary computer module, and electronically send said diagnosing and treatment information back to said primary computer module;

providing mechanisms for relaxation including:
a seat; and a reclining back rest pivotably attached to said seat;
wherein said seat and said reclining back rest are adapted to be connected with said primary computer module and are adapted to stabilize biological vital signs of said patient before said patient's biological vital signs information is collected and sent by said primary computer module;
and a head set adapted to be electrically connected to said primary computer module, wherein said head set includes vibrators and cooling elements adapted to be placed on said patient's head for vibrating and cooling said patient's head; and wherein said head set is adapted to be connected with said primary computer module and is adapted to further stabilize said biological vital signs of said patient before said patient's biological vital signs information is collected and sent by said primary computer module;

providing at least one medical component;
wherein each of said at least one medical component is adapted to be releasably connected to said primary computer module; and
wherein each of said at least one medical component is adapted to obtain and send said patient's biological vital signs information to said primary computer module;

using said data input mechanism of said primary computer module to collect said personal information of said patient;

using said mechanisms for relaxation to stabilize said patient's biological vital signs;

using each of said at least one medical component to obtain and send said patient's biological vital signs information to said primary computer module after using said mechanisms for relaxation to stabilize said patient's biological vital signs;

using said primary computer module to collect said patient's biological vital signs information from each of said at least one medical component after using said mechanisms for relaxation to stabilize said patient's biological vital signs, and send said patient's personal information and said patient's biological vital signs information to said secondary computer module via said electronic communication mechanism; and using said secondary computer module to receive and process said patient's personal information and said patient's biological vital signs information, retrieve said available prior personal information of said patient, and compile and send said diagnosing and treatment information back to said primary computer module via said electronic communication mechanism for said patient to retrieve and use.

27. The method for providing telemedical services of claim 26, further comprising the step of providing and connecting a mechanism for receiving and printing medical prescriptions to said primary computer module.

28. The method for providing telemedical services of claim 26, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

29. The method for providing telemedical services of claim 26, wherein said mechanisms for relaxation further include a foot rest pivotably attached to said seat; and a head rest pivotably attached to said back rest.

30. In an apparatus for providing telemedical services for diagnosing and treating a patient remotely comprising:
   a primary computer module including:
      a data input mechanism;
         wherein said data input mechanism is adapted to allow a patient to input personal information into said primary computer module;
      wherein said primary computer module is adapted to collect said patient's personal information and biological vital signs information of said patient, send said patient's personal information and said patient's biological vital signs information electronically to a secondary computer module, receive diagnosing and treatment information from said secondary computer module, and provide said diagnosing and treatment information to said patient;
   said secondary computer module:
      wherein said secondary computer module is located remotely from said primary computer module, is adapted to retrieve said patient's personal information and said patient's biological vital signs information electronically from said primary computer module, process said patient's personal information and said patient's biological vital signs information, retrieve and process available prior personal information of said patient, and send said diagnosing and treatment information back to said primary computer module;
   an electronic communication mechanism;
      wherein said electronic communication mechanism is adapted to be electronically connected between and communicate with said primary computer module and said secondary computer module, to thereby send said patient's personal information and said patient's biological vital signs information electronically from said primary computer module to said secondary computer module, and electronically send said diagnosing and treatment information back to said primary computer module; and
   at least one medical component;
      wherein each of said at least one medical component is adapted to be releasably connected to said primary computer module; and
      wherein each of said at least one medical component is adapted to obtain and send said patient's biological vital signs information to said primary computer module;
   the improvement comprising mechanisms for relaxation including;
      a seat; and a reclining back rest pivotably attached to said seat;
         wherein said seat and said reclining back rest are adapted to be connected with said primary computer module and are adapted to stabilize biological vital signs of said patient before said patient's biological vital signs information is collected and sent by said primary computer module;
      and a head set adapted to be electrically connected to said primary computer module, wherein said head set includes vibrators and cooling elements adapted to be placed on said patient's head for vibrating and cooling said patient's head; and wherein said head set is adapted to be connected with said primary computer module and is adapted to further stabilize biological vital signs of said patient before said patient's biological vital signs information is collected and sent by said primary computer module;
   wherein said data input mechanism of said primary computer module is used to collect said personal information of said patient;
   wherein said mechanisms for relaxation are used to stabilize said patient's biological vital signs;
   wherein each of said at least one medical component is used to obtain and send said patient's biological vital signs information to said primary computer module after using said mechanisms for relaxation to stabilize said patient's biological vital signs;
   wherein said primary computer module is used to collect said patient's biological vital signs information from each of said at least one medical component after using said mechanisms for relaxation to stabilize said patient's biological vital signs, and send said patient's personal information and said patient's biological vital signs information to said secondary computer module via said electronic communication mechanism; and wherein said secondary computer module is used to receive and process said patient's personal information and said patient's biological vital signs information, retrieve said available prior personal information of said patient, and compile and send said diagnosing and treatment information back to said primary computer module via said electronic communication mechanism for said patient to retrieve and use.

31. The apparatus for providing telemedical services of claim 30, further comprising a mechanism for receiving and printing medical prescriptions to adapted to be connected to said primary computer module.

32. The apparatus for providing telemedical services of claim 30, wherein each of said at least one medical component is chosen from a list of medical components consisting of a blood pressure and pulse rate measuring device, a weight measuring device, a cholesterol measuring device, a pulse rate measuring device, a temperature measuring device, a glucose level measuring device, a spirometer for monitoring and diagnosing asthma symptoms, three-dimensional diagnostic cameras for up close visual inspections, and radiological devices.

33. The apparatus for providing telemedical services of claim 30, wherein said mechanisms for relaxation further include a foot rest pivotably attached to said seat; and a head rest pivotably attached to said back rest.

* * * * *